United States Patent
Zhao et al.

(10) Patent No.: US 11,419,320 B2
(45) Date of Patent: Aug. 23, 2022

(54) COLD-RESISTANT AND LEAN-TYPE TRANSGENIC PIG AND PREPARATION METHOD THEREFOR

(71) Applicant: INSTITUTE OF ZOOLOGY, CHINESE ACADEMY OF SCIENCES, Beijing (CN)

(72) Inventors: Jianguo Zhao, Beijing (CN); Qiantao Zheng, Beijing (CN); Guosong Qin, Beijing (CN); Jing Yao, Beijing (CN); Chunwei Cao, Beijing (CN)

(73) Assignee: INSTITUTE OF ZOOLOGY, CHINESE ACADEMY OF SCIENCES, Beijing (CN)

( * ) Notice: Subject to any disclaimer, the term of this patent is extended or adjusted under 35 U.S.C. 154(b) by 301 days.

(21) Appl. No.: 16/612,142

(22) PCT Filed: Dec. 29, 2017

(86) PCT No.: PCT/CN2017/120153
§ 371 (c)(1),
(2) Date: Nov. 8, 2019

(87) PCT Pub. No.: WO2018/205641
PCT Pub. Date: Nov. 15, 2018

(65) Prior Publication Data
US 2020/0253175 A1    Aug. 13, 2020

(30) Foreign Application Priority Data

May 9, 2017    (CN) .......................... 201710323141.0

(51) Int. Cl.
*A01K 67/027* (2006.01)
*C12N 15/85* (2006.01)
*C12N 15/877* (2010.01)
*C12N 15/90* (2006.01)

(52) U.S. Cl.
CPC ...... *A01K 67/0278* (2013.01); *A01K 67/0275* (2013.01); *C12N 15/8509* (2013.01); *C12N 15/8778* (2013.01); *C12N 15/907* (2013.01); *A01K 2217/052* (2013.01); *A01K 2227/108* (2013.01); *A01K 2267/02* (2013.01)

(58) Field of Classification Search
None
See application file for complete search history.

(56) References Cited

U.S. PATENT DOCUMENTS

2016/0029604 A1    2/2016    Fahrenkrug et al.

FOREIGN PATENT DOCUMENTS

| CN | 101570763 A | 11/2009 |
| CN | 107182940 A | 9/2017 |

OTHER PUBLICATIONS

Berg (PLoS Genetics, Aug. 2006, vol. 2, p. 1178-1181).*
Auer, O Thomas et al., "Highly efficient CRISPR Cas9-mediated knock-in in zebrafish by homology-independent DNA repair", Cold Spring Harbor Laboratory Press, pp. 142-153.
Frida, Berg et al., "The Uncoupling Protein 1 Gene (UCP1) Is Disrupted in the Pig Lineage: A Genetic explanation for Poor Thermoregulation in Piglets", PLoS Genetics, Aug. 2006, vol. 2, issue 8, pp. 1178-1181.
Jastroch, Martin and Andersson, Leif, "When Pigs fly, UCP1 makes heat", Molecular Metabolism 4, 2015, pp. 359-362.
Liu, Chousheng, "Regulation Gene of the Skeletal Muscle Growth in Animals and the Adipose Aggradation in Pigs", No. 2, Feb. 29, 2004, pp. 1-109.
Zheng, Fang et al., "Transgenic Pig Technology and Its Application in Agriculture", Acta Veterinaria Et Zootechica Sinica, Feb. 15, 2016, pp. 218-224.
International Search Report dated Mar. 30, 2018 in connection with PCT International Application No. PCT/CN2017/120153.
Written Opinion (form PCT/ISA/237) dated Mar. 30, 2018 in connection with PCT International Application No. PCT/CN2017/120153.

* cited by examiner

*Primary Examiner* — Michael C Wilson
(74) *Attorney, Agent, or Firm* — John P. White (57) ABSTRACT

Disclosed is a cold-resistant and lean-type transgenic pig and a preparation method therefor, which relate to the field of genetic engineering. By transferring a mouse uncoupling protein 1 gene into the genome of a pig, a transgenic pig is obtained which can not only resist the cold but also have an increased lean meat rate by reducing fat deposition. Simultaneous improvement of two important production traits of pigs through the site-directed single gene manipulation not only lays a foundation for the application and basic research of genetic editing for big animals, but also provides with breading researchers a new way of thinking for improving traits of livestock.

5 Claims, 3 Drawing Sheets

Specification includes a Sequence Listing.

Figure 6

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial sequence
<220> FEATURE:
<223> OTHER INFORMATION: Laboratory synthesis

<400> SEQUENCE: 1
cctccggtac cattcggtac aaa                                        23

<210> SEQ ID NO 2
<211> LENGTH: 924
<212> TYPE: DNA
<213> ORGANISM: Mus musculus

<400> SEQUENCE: 2
atggtgaacc cgacaacttc cgaagtgcaa cccaccatgg gggtcaagat cttctcagcc    60
ggagtttcag cttgcctggc agatatcatc accttcccgc tggacactgc caaagtccgc   120
cttcagatcc aaggtgaagg ccaggcttcc agtaccatta ggtataaagg tgtcctaggg   180
accatcacca ccctggcaaa aacagaagga ttgccgaaac tgtacagcgg tctgcctgcg   240
ggcattcaga ggcaaatcag ctttgcctca ctcaggattg gcctctacga ctcagtccaa   300
gagtacttct cttcagggag agaaacacct gcctctctcg gaaacaagat ctcagccggc   360
ttaatgactg gaggtgtggc agtgttcatt gggcagccta cagaggtcgt gaaggtcaga   420
atgcaagccc agagccatct gcatgggatc aaacccgct acacggggac ctacaatgct    480
tacagagtta tagccaccac agaaagcttg tcaacacttt ggaaagggac gacccctaat   540 ctaatgaaa atgtcatcat caattgtaca gagctggtaa catatgacct catgaagggg    600
gcccttgtaa acaacaaaat actggcagat gacgtcccct gccatttact gtcagctctt    660
```

```
gttgccgggt tttgcaccac actcctggcc tctccagtgg atgtggtaaa aacaagattc      720
atcaactctc tgccaggaca gtacccaagc gtaccaagct gtgcgatgtc catgtacacc      780
aaggaaggac cgacggcctt tttcaaaggg tttgtggctt cttttctgcg actcgggtcc      840
tggaacgtca tcatgtttgt gtgctttgaa cagctgaaaa agagctgat gaagtccaga       900 cagacagtgg attgtaccac ataa                                             924

<210> SEQ ID NO 3
<211> LENGTH: 6716
<212> TYPE: DNA
<213> ORGANISM: Mus musculus

<400> SEQUENCE: 3
cgctagtgta tgcaatggtg tcagcgtttg gaagctgatt atgggatgga tccctggata      60
tggcaatcac tagatggtct atccttttgt cacagctcca aattttgtct ctgtaactcc      120
ttccatgggt gttttgttcc catttctaag aaggggcaaa gtgtccacac tttggtcttt      180
gttcttcttg agtttcatgc gtttagcaaa ttgtatctta tcttgggt attctaaatg        240 tctgggctaa tatccactta tcagtgagta catattgtgt gagttccttt gtgattgggt      300
tacctcactc aggatgatgc cctccaggtc tatccatttg cctaggaatt tcataaattc      360
attcttttta atagctgagt agtactccat tgtgtaaatg taccacattt ctgtatccat      420
tcctctgttg aggggcatct gggttctttc cagcttctgg ctattataaa taaggctgct      480
atgaacatag tggagcatgt gtccttctta ctggttggga catcttctgg atatatgccc      540
aggagaggta ttgtgggatc ctccggtagt actatgtcca attttctgag gaaccgccag      600
actgatttcc agagtggttg tacaagcttg caatcccacc aacaatggag gagtattcct      660 cttctccac atcctcgcca gcatctgctg tcacctgaat ttttgatctt agccattctg       720
actggtgtga ggtggaatct cagggttgtt ttgatttgca tttccctgaa ggtccctact      780
atttatctaa cattttgaat gcaacattct ttcctttgta catagtcata tgccatgtgc      840
attagtaatc tgctataata cagcccaac gatgagacga ctcagacaaa agagtgtatt       900
tgtatctctt gtgacatcta ggatatagg gaagaaacac tccacacagt tatgcagggc       960
tctctgtttt gttttgtttt taaagattta ttttatttca tttattttat gtatataaaa      1020
tacatgaaat gagtacactg tagctatact gatggttgtg agccatcatg tggtttctgg      1080
gaattagaat tcagggcctc tgcttgctct agttggctcc agttgctcca gtctaaagat      1140
ttatttatta ttagatctaa gtacattgta gctgtcttca aacacaccag aagagggcat      1200
aggatcccat tacagatggt tgtgagccac catgtggttg ctgggatttg aactcaggac      1260
ctctggaaga gcagtcagtg ctcttaactg ctgagccatc tctccagccc ttagcctgct      1320
ctcttatatc atctatgagc acctgtctat ggtaacagca ccacaatggg ctggacctta      1380
cctcctcaat catcaagcaa gaaaacgtcc cataggcttg cccacagggc agtctggtgg      1440
gagcatttcc ccaactgatg ttctctcccc aaatgactta tctgatacac tggccttcgg      1500
agaaaagcaa gtcaacacct cattgtgatc ccattttacc cagtcagaat gtcataagaa      1560 acaaataac attttcataa gaaaataaac aacaatacat tctgtcaagg atgtagacag       1620
atgggatgca cttgattcac tgctggtggg aatgataact agtccaatct cagtggaagt      1680
cagtctggag tgttctcaga aaatgaaaaa atagctgggc agtggtggca gatgccttta      1740
atcccagcac ttgggaggca gaggcaggtg gatttctgag tttgaggcca gccttgtcta      1800
```

```
cagagtgagt tccaggacag ccaaggctac acagagaaac cctgtctcaa aaaaccaaaa    1860
aaaagccgga cgtggtggcg cacgccttta atcccagcac tcgggaggca gaggcaggcg    1920
gatttctgag ttcgaggcca gcctggtcta cagagtgagt tccaggacag ccagggctac    1980
acagagaaac cctgtctcga aaaccaaaa  aaaaaaaaa  aaaaaaaaaa aggaagtgaa    2040
gaatagctgt ggataacaca gcttttcttt tctttatatt tcaggcatca gggatagagg    2100
tcaggtgtca atgtaaatca ctctaccact gagttacact tctaaattaa agacattttt    2160
cctttcttga atgcccaaaa atttggagta ctgcaggaca ggctcactct tctgcagtta    2220
gtgttatgtc tcaaaatttg atttgaggtt tagttgtttc agtaaattgt cttttaaag    2280
tcatgactaa acaataatat acagtgaaat ttaaccacat tcaggaaaca ctgaggaaac    2340
tcaggcctgt ggggaaatct ggccttttgt ttaagtatct cacttcgcat gtaggcgaga    2400
attgagatgt gaacatgagc tcctgaagga aaggaccacg tttctgtggc tgcttcactc    2460
tgggcagtaa cacatctgtc caggtaaacc cagccttgct gaacgtcaat ctcagcactt    2520
gggaggcaga ggtgagagtt tgaggccagt ctgatctata gagcaagttc caggatagct    2580
tgggctacac tgaaaaaaca ctgtcttgaa aaacaaaaca aaacaaaaca aaacaaaaca    2640
aaacaaaaca aaacaccaaa aaccaaaaaa gaaaaaaaaa aacaggaaaa gaaagaaaa    2700
aaatcaaaat aaaacaaagc caaaaacaaa gcaaaaaaaa aaaccaccca gcaaaaaacc    2760
aaaccgccta gcctcaagac atgtgtggtt gaatgttttt cacttctagt cgctaagcaa    2820
gtgtgtgttt ttacacaatg ccctctgtgg tgagtggcgg attcccctga gagttcacca    2880
aatgataggc tttcacaatg ctcccgggtg tctaccagac ccagcaaagt attgatgtgg    2940
ttttggggtg aaagtcactc tgtcttgtgc aatagttaga atctgctgaa accagcagtg    3000
ttcctatatg ggacaggggt ccagagctaa cccggaggct ataactgagc agaggtgaag    3060
accacgaggc attggggagc gtatgccctt tgtggtcaga gagatctagc ttcgtgcctt    3120
gggtctgtgt ctctccctct tactggcttc tggcttcttc attaagtggg agacaaccac    3180
aggtatctgt atgggaagac tcgactaccc cttgactcaa cattgcttgt tacttacttt    3240
gtacaagata ctacttagtc taggggttat ggagcataac ctcaagtagg taaagccccct    3300
gctccagcgt gtttgcattc cagtaagaag cgaaagacag taacacacat acaaaataag    3360
taagaaaatg caacaacagc aacaacaaca acacacacac acaaagtaag caaaacgcta    3420
agggaaagat agagagtgat acagctttga gttgctgtag ttcttctctc tccttttgctt    3480
catacagttt gcttgggaag tgtccagggc catggggtca caactaacag cccttggaaa    3540
tgagcttgtg tccttaatct tcatgaccta acgtgatttc tctagaaaca tcagtgcatt    3600
aacaggaaga caagatggaa gatcatattt tggctctcct tccttggtgg gttgacactg    3660
ctggtcctat ccactagtaa aagcatgact cttaggctct gtgtggccag tggaaggtgg    3720
cagtggagg aagcagatgc ttggccagcc tttgcctggg agcagtctag ctctgagtgt    3780
cttattggag cagctgctgg catccagagt tcttttttgga ttcacgattt aattcaaaag    3840
ctttgtgctc ccgagaatca gctctggtct ttcaaaaata agatgtgagt ccgccgagag    3900
gctcccaagg tattgccttg ccaactgcaa gccttttagg agcagtttag tgagtggtga    3960
ctgctagttg cagttggctg ttagcccaga gctaataata gatagaaaag gtatatactt    4020
aaggagtctg gaaactgagg tttatctact cacagaaaat gagttctaa  aaaactagct    4080
tgaaacttac ccagaaaaat cttagaacat ggttctccaa tgtcaaggta agtgttctgt    4140
gacactgggc ttgaattatg tagggaccac agattttaga atttggaccc ctgaacttgc    4200
```

```
ttcacacccc accaggaacc ttcctgtaca acagccctca gaattcatct acatggtctt    4260
ttctcagtat gggatccggt ctagcaagtg gagcacacct tctattgctt aaagatttgt    4320
ttatgtatat gggtattttg gctgcatgca tatttgcaca ccaaaagaag gcagcggatc    4380
ccatggaatt actgtgggtg ctgggaattg aactcaggac ctctggaaga atagccagtg    4440
ctcttaacca ctgagccatg cctgcagtcc atctattttt tattctagta cagcccctct    4500
tcattcttac tgaaatagta atgcctgaac cacacagctt cacatttagt tacaaagaaa    4560
gagtgggagt atcatgtgac aattagtgtt gttgactctc caggacaaac ttatgggaaa    4620
gggaggtctc ctgacccctg aacaatcatt ttacttgagg ataattttca ttgcactcag    4680
aaacatgctg aattattgtc cttacccttg ccccatctct tgctctggta gagaatggcc    4740
aaagcctgga acaggatgg cttgacagaa gctctacttg gcttcccaga cccaagctgg    4800
attaaaccag gttccctaag gagtcttaag gcagctgcca ggagcaaggg gcccactcat    4860
tggctattgg ccttgactgg gttggccaat ggtaagctgg ggtctgcctg tccccatgag    4920
taccagacta atgagacctg gccactttct cctcatttct gtctgtacga ttgtcagtgg    4980
atctgacgac accaaaaggt aagaacaatt ctatattctc ggctggctgg gtatgaatgc    5040
agaatcccac ttgggctgtg ttcagatttt gctctctgca gcagtgtgaa ggtagatgtt    5100
gagaaaactc aggccttgga acatggttg gggcagataa gctttgggc ttttctttaa    5160 ctcttcaaag ctctaagaaa gaaacaataa cctttcggtc cacaagcttg agcctaacgg    5220
tgtctgttca cagcagtaaa accccaacta agacactgat gaagacctcc tgggagagtg    5280
agggctgggt agccactgaa ggctctctgg gagaggcgag tatgtagatg cagatctttg    5340
gagtggattc cacttagcta tataggacat gatgcaggtc ctgattggat gtgccatgtg    5400
agtctgcctt tcccatgact attcacctgt caatttcagg gctcaggata ctactgttgc    5460
aagctctcct gttcctctta actcgacggt atcgatacca ccccatcgat aagcttgata    5520
tcgaattcct gcagcccggg ggatcctgag aacttcaggg tgagtttggg gacccttgat    5580
tgttctttct ttttcgctat tgtaaaattc atgttatatg gaggggcaa agttttcagg    5640 gtgttgttta gaatgggaag atgtcccttg tatcaccatg gaccctcatg ataatttgt    5700 ttctttcact ttctactctg ttgacaacca ttgtctcctc ttattttctt ttcattttct    5760 gtaactttt cgttaaactt tagcttgcat ttgtaacgaa ttttttaaatt cacttttgtt    5820 tatttgtcag attgtaagta ctttctctaa tcacttttttt ttcaaggcaa tcagggtata    5880
ttatattgta cttcagcaca gttttagaga acaattgtta taattaaatg ataaggtaga    5940
atatttctgc atataaattc tggctggcgt ggaaatattc ttattggtag aaacaactac    6000
accctggtca tcatcctgcc tttctcttta tggttacaat gatatacact gtttgagatg    6060
aggataaaat actctgagtc caaaccgggc ccctctgcta accatgttca tgccttcttc    6120
tctttcctac agctcctggg caacgtgctg gttgttgtgc tgtctcatca ttttggcaaa    6180
ggattcactc ctcaggtgca ggctgcctat cagaaggtgg tggctggtgt ggccaatgcc    6240
ctggctcaca ataccactg agatcttttt ccctctgcca aaaattatgg ggacatcatg    6300
aagccccttg agcatctgac ttctggctaa taaggaaatt tattttcat tgcaatagtg    6360 tgttggaatt ttttgtgtct ctcactcgga aggacatatg ggagggcaaa tcatttaaaa    6420
catcagaatg agtatttggt ttagagtttg gcaacatatg cccatatgct ggctgccatg    6480
aacaaaggtt ggctataaag aggtcatcag tatatgaaac agcccctgc tgtccattcc    6540
```

```
ttattccata gaaaagcctt gacttgaggt tagatttttt ttatattttg ttttgtgtta      6600 ttttttctt taacatccct aaaatttcc ttacatgttt tactagccag atttttcctc        6660
ctctcctgac tactcccagt catagctgtc cctcttctct tatggagatc cctcga         6716
```

COLD-RESISTANT AND LEAN-TYPE TRANSGENIC PIG AND PREPARATION METHOD THEREFOR

CROSS-REFERENCE TO RELATED APPLICATIONS

This application is a § 371 national stage of PCT International Application No. PCT/CN2017/120153, filed Dec. 29, 2017, claiming priority of Chinese Patent Application No. 201710323141.0, filed May 9, 2017, the entire contents of each of which are hereby incorporated by reference herein into the application.

REFERENCE TO A SEQUENCE LISTING

This application incorporates-by-reference nucleotide and/or amino acid sequences which are present in the file named "200414_91207_Substitute_Sequence_Listing_CAS.txt", which is 10.4 kilobytes in size, and was created Apr. 14, 2020 in the IBM-PC machine format, having an operating system capacity with MS-Windows, which is contained in the text file being filed Apr. 14, 2020 as part of this application.

TECHNICAL FIELD

The present invention relates to the field of genetic engineering, in particular to a cold-resistant and lean-type transgenic pig and a preparation method thereof.

BACKGROUND ART

In the modern breeding work of pigs, breeding researchers have been working on reducing the excessive deposition of fat, increasing the lean meat rate and improving the feed conversion efficiency. There are also many fat-type local varieties in China, such as Guangxi Luchuan pigs and Taihu pigs, which need to be improved to increase the lean meat rate and feed conversion rate.

At present, the improvement of important economic traits of pigs mainly depends on the method of genetic breeding. The breeding work has undergone a process from conventional breeding depending on quantitative genetics to molecular marker-assisted selection (MAS) and direct selection of genotype or quantitative trait locus (QTL) depending on genomics and molecular biology. Although the conventional breeding method has made great progress in the improvement of production traits of pigs, this process requires the measurement techniques and breeding methods to be quite scientific, accurate and feasible, and requires a lot of manpower and material resources, and the breeding cycle is long. Molecular breeding is also facing a lot of problems, especially when facing quantitative traits with low heritability, identification of trait-related genes often takes a long time with relatively high cost, and many studies ultimately only stays at targeting gene location, without further progress towards breeding applications.

Not only that, the capacity of shivering thermogenesis of newly born piglets is still not perfect, and the survival rate will be reduced due to poor thermogenesis capacity. In modern farms, heat preservation lamps are used to keep the piglets warm to improve the survival rate. However, the use of heat preservation lamps undoubtedly increases production costs, and for some farmers who do not have heat preservation lamps in some cold areas, the survival rate of piglets is bound to be affected by the cold weather.

Therefore, there is an urgent need to provide a method that can improve the lean meat rate and feed conversion rate of pigs, and improve the cold resistance of pigs.

Studies have found that uncoupling protein 1 (UCP1) is a protein that is specifically expressed in brown fat and is present on the mitochondrial inner membrane. It can eliminate the proton concentration difference between the two sides of the mitochondrial inner membrane due to the electron transfer of the respiratory chain, so that the electrochemical concentration potential energy can be dissipated in the form of heat, which is also known as non-shivering thermogenesis. However, pigs do not contain brown fat and are lack of functional UCP1 gene (Jastroch, M., & Andersson, L. When pigs fly, UCP1 makes heat. Molecular Metabolism, 4(5), 359-362. doi:10.1016/j.molmet.2015.02.005). Therefore, no reports have been published on the application of this gene to the improvement of pigs.

SUMMARY OF THE INVENTION

In order to solve the problems in the prior art, the purpose of the present invention is to provide a cold-resistant and lean-type transgenic pig and a preparation method thereof.

In order to achieve the purpose of the present invention, the technical solutions of the present invention are as follows:

In a first aspect, the present invention provides a cold-resistant and lean-type transgenic pig, wherein the pig is a transgenic pig in which a UCP1 gene is expressed in adipose tissue.

The UCP1 gene may be selected from functional UCP1 genes in any species, such as human, bovine, caprine, and mouse.

Further, the UCP1 gene is a mouse uncoupling protein 1 gene, and the expression of the UCP1 gene is specifically driven by an adiponectin promoter.

Preferably, the adiponectin promoter is a mouse adiponectin promoter.

The UCP1 gene and the promoter in a donor plasmid of the present invention are obtained from a Pcdna3.1 vector containing a mouse adiponectin promoter and a UCP1 coding sequence by enzyme digestion, and the nucleotide sequences thereof are represented by SEQ ID NO. 2 and SEQ ID NO. 3, respectively.

In a second aspect, the present invention also provides a preparation method of the aforementioned transgenic pig, comprising the following steps:

S1. constructing a donor plasmid comprising a target sequence, an adiponectin promoter and an UCP1 gene;

S2. constructing a Cas9/gRNA vector targeting the target sequence;

S3. co-transfecting the constructed donor plasmid and the Cas9/gRNA vector into porcine fetal fibroblasts, obtaining monoclonal cells by limiting dilution method, and further obtaining successfully targeted positive cells by PCR genotyping; and S4. using positive colony cells obtained by screening as donor cells of nuclear transfer, and isolated oocytes as recipient cells of nuclear transfer, and performing somatic cell cloning by nuclear transfer technology to obtain the transgenic pig.

The starting vector of the donor plasmid can be a vector conventionally used in the art. In a specific embodiment of the present invention, a pLB vector is selected as the starting vector.

The target sequence in the donor plasmid is located before the promoter sequence and the UCP1 gene is located after the promoter sequence. The target sequence was designed using the online tool CRISPR Design Tool (http://crispr.mit.edu/) developed by Professor Zhang Feng of the Massachusetts Institute of Technology and synthesized by Thermo Fisher, its nucleotide sequence is represented by SEQ ID NO. 1, and the target sequence is located in the exon 2 of the pig uncoupling protein 1 pseudogene in the pig genome.

The Cas9/gRNA vector is prepared according to conventional technical means in the art. The PX330 plasmid containing Cas9 was purchased from Addgene. The PX330 plasmid was first cut with BbsI endonuclease, and the linearized plasmid was purified and recovered. Then, the gRNA recognition sequence (i.e., the aforementioned target sequence) was subjected to denaturation and renaturation treatment to change from a single-stranded nucleotide to a double-stranded oligonucleotide, and then the double-stranded DNA was ligated to the linearized PX330 plasmid using T4 DNA ligase. Transformation, spreading the obtained bacteria solution onto a plate and cultivation were performed, followed by further sequencing to identify positive bacterial, and performing large-scale extraction of plasmids for later use.

In a third aspect, the present invention provides the use of the aforementioned method for improving the cold resistance of a transgenic pig, and/or increasing the lean meat rate of a transgenic pig, and/or increasing the feed conversion rate of a transgenic pig.

The raw materials or reagents involved in the present invention are all commercially available products, and the operations involved are routine operations in the art unless otherwise specified.

Based on the common knowledge in the art, the above various preferred conditions can be combined with one another to obtain a specific embodiment.

The beneficial effects of the present invention lie in that:

The present invention obtains a transgenic pig which can resist the cold stimulation and have reduced fat deposition and increased lean meat rate by transferring the uncoupling protein 1 gene of a mouse into the genome of a pig.

The present invention provides a transgenic pig which can not only resist the cold but also have an increased lean meat rate by reducing fat deposition. In the present invention, simultaneous improvement of two important production traits of pigs through the site-directed single gene manipulation not only lays a foundation for the application and basic research of genetic editing for large animals, but also provides with breeding researchers a new way of thinking for improving traits of livestock.

SPECIFIC MODES FOR CARRYING OUT THE EMBODIMENTS

The preferred embodiments of the present invention will be described in detail below with reference to Examples. It is to be understood that the following Examples are presented for illustrative purposes only and are not intended to limit the scope of the present invention. Various modifications and alterations of the present invention can be made by a person skilled in the art without departing from the purpose and spirit of the present invention.

The UCP1 expression vector Pcdna3.1 driven by the mouse adiponectin promoter was obtained by cloning the mouse adiponectin promoter and the UCP1 coding sequence into the Pcdna3.1 plasmid backbone. Sequence determination and primer synthesis were performed by Thermo Fisher Co., Ltd. Taq enzyme, T4 DNA ligase and endonuclease were purchased from Beijing NEB Co., Ltd., and the reagents for somatic cell nuclear transfer were purchased from Sigma company. For conventional experimental procedures such as enzyme digestion, ligation, recovery, transformation, and PCR amplification, refer to *Molecular Cloning* (Third Edition).

The experimental methods used in the following Examples are conventional methods unless otherwise specified.

The materials, reagents and the like used in the following Examples are commercially available unless otherwise specified.

Example 1: Preparation of a Transgenic Pig

Figure 1:
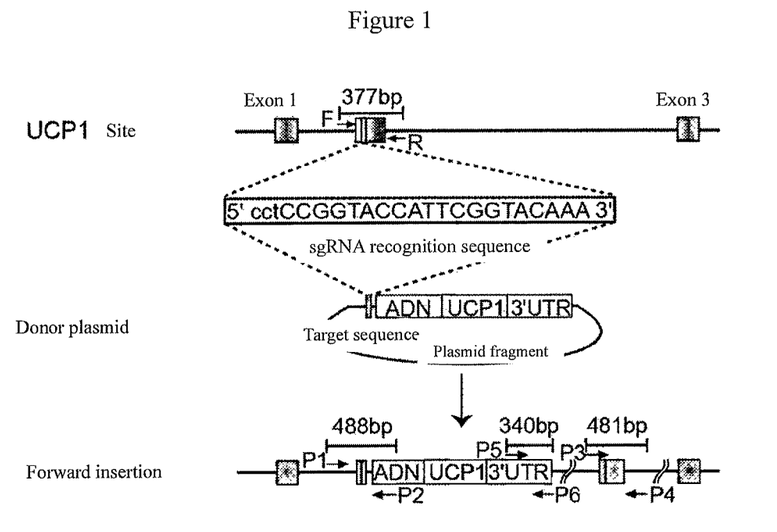
FIG. 1 shows the strategy of the targeting vector construction, and identification of gene knock-in in the present invention.

The construction of a targeting vector and the knock-in of an exogenous gene were carried out according to the strategy described in FIG. 1.

1. Construction of Cas9/gRNA Targeting Vector

The gRNA recognition sequence was designed using the online tool CRISPR Design Tool (http://crispr.mit.edu/) developed by Professor Zhang Feng of the Massachusetts Institute of Technology and synthesized by Thermo Fisher company, and the gRNA recognition sequence was located in the exon 2 of the pig uncoupling protein 1 pseudogene. The PX330 plasmid containing Cas9 was purchased from Addgene. The PX330 plasmid was first cut with BbsI endonuclease, and the linearized plasmid was purified and recovered. Then, the gRNA recognition sequence was subjected to denaturation and renaturation treatment to change from a single-stranded nucleotide to a double-stranded oligonucleotide, and then the double-stranded DNA was ligated to the linearized PX330 plasmid using T4 DNA ligase. Transformation, spreading the obtained bacteria solution onto a plate and cultivation were performed, followed by further sequencing to identify positive bacterial, and performing large-scale extraction of plasmids for later use.

2. Construction of an Uncoupling Protein 1 Donor Plasmid

Firstly, the Pcdna3.1 plasmid was double-enzyme digested using Kpn I endonuclease and Xho I endonuclease, and the adiponectin promoter-UCP1 fragment was recovered by electrophoresis. The adiponectin promoter-UCP1 fragment was ligated to the pLB vector using the pLB Zero-Background Simple Fast Cloning Kit (TIANGEN BIOTECH Co., Ltd.), the positive plasmid was identified, and large-scale extraction of the plasmid was performed for later use. Finally, the obtained new plasmid was single-enzyme digested using BspEI enzyme, purified and recovered, and then, the gRNA recognition sequence with BspEI restriction enzyme cutting site, i.e., the target sequence (Bait sequence), was ligated to the linearized plasmid using T4 DNA ligase to obtain the donor plasmid.

3. Acquisition of UCP1 Transgenic Fibroblasts 3.1 Construction of Porcine Fetal Fibroblasts 1) A Bama sow at day 35 of gestation was killed to give the uterus, and the uterus was transported to the laboratory within 1 hour. The fetus was taken out from the uterus, washed with DPBS containing antibiotics, transferred to a clean bench, and the head, limbs and viscera were removed using ophthalmic scissors. The remainder was washed with DPBS repeatedly until it was clean. The remainder was cut into pieces using ophthalmic scissors in a 100 mm culture dish.

2) The shredded tissue was transferred to a new 100 mm culture dish, followed by addition of 10 mL of a digestive solution and digestion in a 5% $CO_2$ incubator at 37° C. for 4 to 6 h. The components of the digestive solution comprise: DMEM high glucose medium (Gibco) supplemented with 15% fetal bovine serum (Hyclone), 0.032% collagenase IV (Sigma), 25 Kunitz units/mL DNase I (Sigma) and 40 μg/mL gentamicin (Sigma). After the digestion was completed, the digested product was collected, and centrifuged at 3000 rpm for 10 min in a centrifuge tube, followed by discarding the supernatant, resuspending the resultant pellet with a culture medium and then centrifuging. Finally, the resuspended tissue was placed in a 25 $cm^2$ culture dish. The components of the culture medium comprise: DMEM high glucose medium (Gibco) supplemented with 15% fetal bovine serum (Hyclone) and 40 μg/mL gentamicin (Sigma).

3) Subculture or Cryopreservation was Carried Out when Cells Grow to 80% Confluence.

3.2 Transfection of Fetal Fibroblasts with the Targeting Vector

The fetal fibroblasts were resuscitated two days before transfection in a 25 $cm^2$ culture dish. Transfection can be carried out when the cells grew to about 70% confluence, and the culture medium was replaced 4 h before transfection. The cells were digested using 0.25% trypsin (Invitrogen), resuspended with an electrotransfer solution, and the Cas9/gRNA plasmid and the donor plasmid were added to the resuspended cells. Transfection was carried out with a nuclear electroporation apparatus (Nucleofector 2b Device, Lonza) using U-023 procedure. The transfected cell suspension was transferred to a 60 mm culture dish and cultured for 48 hours.

3.3 Cell Screening and Genotyping

Figure 2:
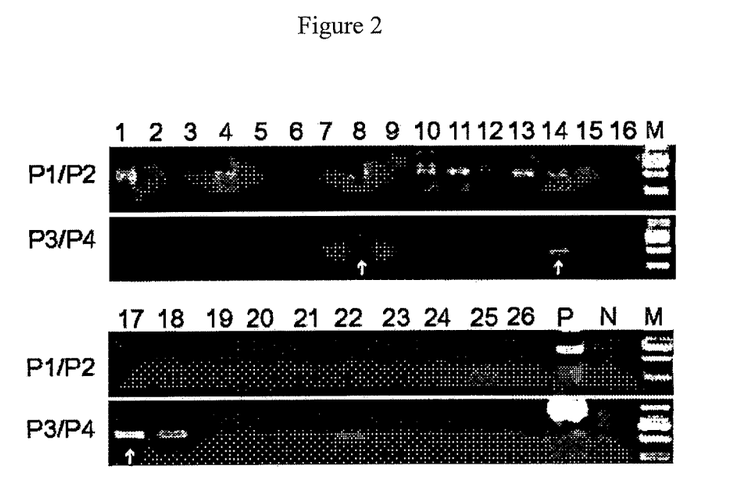
FIG. 2 shows the genotyping of positive targeted cells of the present invention.

The cells were digested using 0.25% trypsin (Invitrogen). After the digestion reaction was terminated, the cell density was measured using a hand-held automatic cell counter (Millipore). The cells were inoculated into a 96-well plate using limited dilution method according to the cell density. Then, 100 ul of culture medium was added to each well and only one cell was contained per 100 ul of culture medium. After 3-4 days, the culture medium was replaced. When the cells growed to one hundred percent confluence of the 96-well plate, they were transferred to a 24-well plate. When cells growed to one hundred percent confluence of the 24-well plate, a part of the cells was transferred to a 6-well plate, and a small portion of the cells was further cultured in the 24-well plate for genotyping. Finally, a total of 26 cell colonies were obtained and identified by PCR. It was found that cell colonies with bands at both the 5' junction end and the 3' junction end are transgenic, wherein the colony Nos. 8, 14 and 17 are positive (FIG. 2) for subsequent experiments.

4. Preparation of a Nuclear Transfer Embryo and a Cloned Pig 4.1 Maturation Culture of Pig Oocytes:

The ovaries of pig collected from a slaughterhouse were placed in a thermos containing physiological saline comprising penicillin and streptomycin at 37° C., and transported to the laboratory within 1 hour. After washing the ovaries with physiological saline for 3 to 5 times, the follicles with a diameter of 3 to 8 mm on the ovary surface were aspirated with syringes, and the follicular fluid containing oocytes was collected in a 50 mL centrifuge tube and washed with TL-HEPES oocyte-washing liquid for 3 times. Dense cumulus-oocyte complexes (COCs) with uniform cytoplasm containing more than three layers of cumulus cells were selected under a stereomicroscope and transferred into an in-vitro maturation culture solution, and cultured under conditions of 39.0° C. and 5% $CO_2$ for 42 to 44 h.

4.2 Acquisition of a Reconstructed Embryo:

The oocytes subjected to in-vitro maturation culture for 42 to 44 h were digested with 0.1% hyaluronidase (purchased from Sigma company) to remove the cumulus cells around the oocytes. Under a stereomicroscope, oocytes with uniform cytoplasm, obvious perivitelline space and the first polar body expelled, i.e. MII stage oocytes, were selected and placed in a micro operation drop, the mature oocytes were fixed with a fixing tube such that the polar body was at the direction of 3 o'clock, and the first polar body and about ⅛ of the surrounding cytoplasm (including nucleus) were sucked out with an enucleation needle having an outer diameter of 20 μm. The UCP1 transgenic fibroblast was injected into the perivitelline space of the enucleated oocyte, so that the donor cell was in contact with the oocyte membrane. Then, the oocyte was fused with the donor cell by an electric activation method (BTX Electro-cell Manipulator 200) to obtain a reconstituted embryo. The reconstituted embryo was placed in PZM3 solution, cultured under conditions of 39.0° C. and 5% $CO_2$ for 14 to 16 h, and then embryo transfer was performed.

4.3 Embryo Transfer:

The reconstituted embryos having been subjected to in-vitro culture for 14 to 16 h were transferred into the fallopian tubes of pseudo-pregnant sows in synchronous estrus, and about 180 embryos were transferred to each sow on average. After 28 days, the sows were examined for pregnancy by ultrasound. If a pig was pregnant, the pregnancy status was monitored every two weeks by ultrasound. The present invention obtained 3 pregnant sows and 12 piglets were successfully delivered.

5. Genotyping of UCP1 Gene Knock-in Pigs

Figure 3:
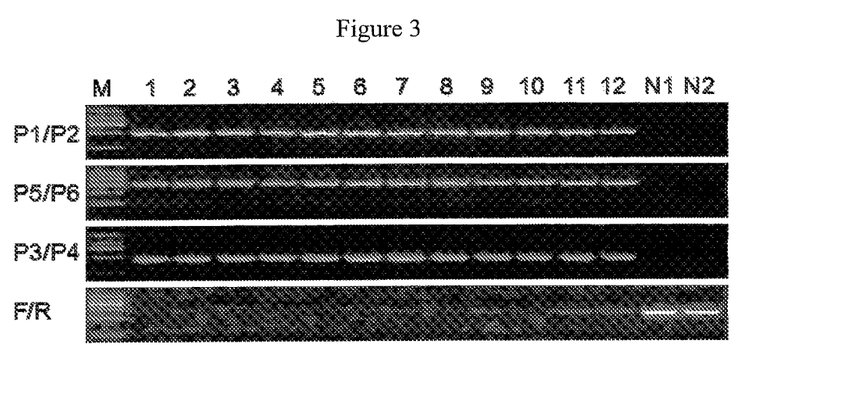
FIG. 3 shows genotyping of the transgenic pig of the present invention.

After the pig was born, the ear tissue was taken and DNA was extracted using a genomic DNA extraction kit (TIANGEN BIOTECH Co., Ltd.) for PCR genotyping (FIG. 3).

Example 2: Detection of Cold Resistance of Piglets

Figure 4:
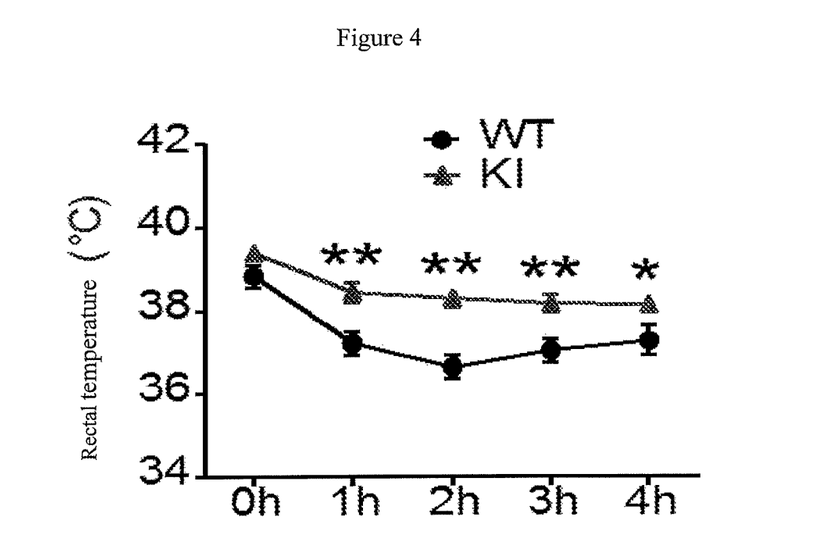
FIG. 4 is a graph showing changes in the rectal temperature of the pig under the cold condition of the present invention.
Figure 5:
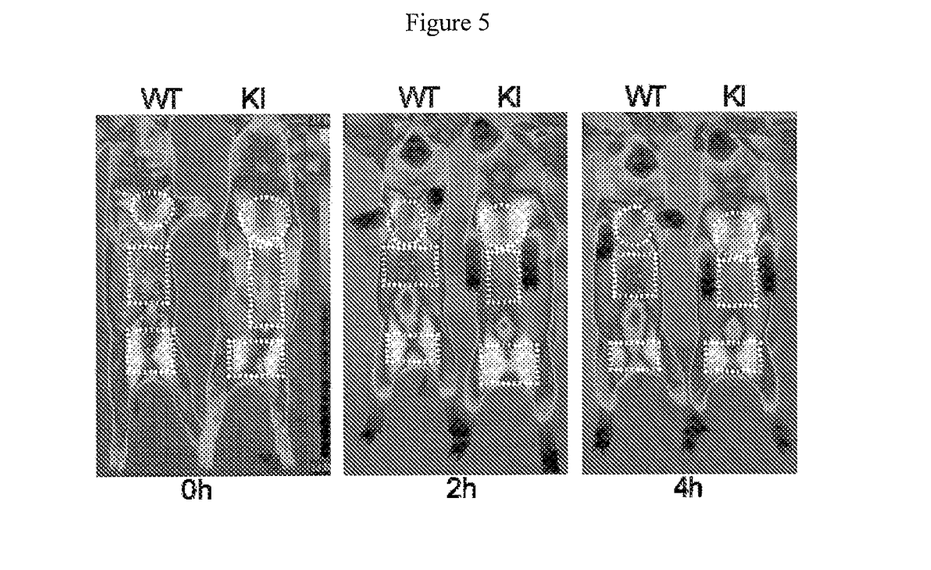
FIG. 5 shows the infrared photograph and body surface temperature of the pig under the cold condition of the present invention.

One-month-old transgenic pigs and wild-type pigs were placed in a refrigerator at 4° C. for 4 h. Starting from 0 h, the rectal temperature of pigs was measured by an electronic thermometer (Tianjin Jinming Instrument Co., Ltd.) every 1 hour (FIG. 4). It can be seen from FIG. 4 that the rectal temperature of the transgenic pig was significantly higher than that of the wild-type pig during 1 h to 4 h of cold stimulation. At the same time, the pigs were photographed with an infrared camera (FUR) to record changes in the temperature of the pig's body surface (FIG. 5). It can be seen from FIG. 5 that after cold stimulation, the infrared color of the transgenic pig was significantly stronger than that of the wild-type pig, that is, the temperature of the transgenic pig in the area marked with white line was higher than that of the wild-type pig.

Example 3: Slaughter Index Measurements

Figure 6:
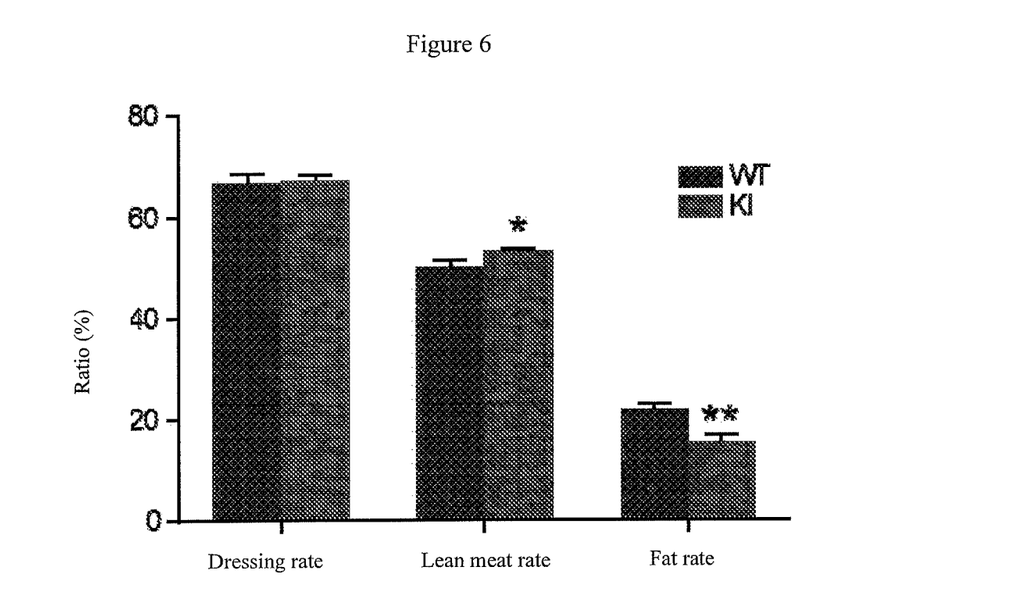
FIG. 6 shows measurements of slaughter indexes of the wild-type pig and the transgenic pig of the present invention.

The slaughter experiment was carried out when the pigs were 6 months old. Fasting for 24 hours was performed before slaughtering. The pigs were weighed before slaughtering, subjected to anesthesia and killed by bloodletting. The head, hooves, tail and viscera were removed with retained kidney and leaf fat, and then carcass weight was weighed and recorded. The ratio of the carcass weight to the weight before slaughtering is the dressing rate. The pig carcass was separated from the middle. For the left carcass, lean meat, fat, skin and bone were separated and weighed, respectively, and the proportion of each part in the total was calculated (see FIG. 6). It can be seen from FIG. 6 that there is no difference in the dressing rate between the wild-type pig and the transgenic pig, while the lean meat rate of the transgenic pig is significantly higher than that of the wild-type pig and the fat rate is significantly lower than that of the wild-type pig.

Although the present invention has been described in detail with the general description and the specific embodiment, it is obvious to a person skilled in the art that some modifications or improvements can be made on the basis of the present invention. Therefore, these modifications or improvements made on the basis of without departing from the spirit of the present invention are intended to be within the protection scope of the present invention.

INDUSTRIAL APPLICABILITY

The present invention provides a cold-resistant and lean-type transgenic pig and a preparation method therefor. In the present invention, by transferring a mouse uncoupling protein 1 gene into the genome of a pig, a transgenic pig is obtained which can not only resist the cold but also have an increased lean meat rate by reducing fat deposition. The transgenic pig provided in the present invention can not only resist the cold but also have an increased lean meat rate by reducing fat deposition. In the present invention, simultaneous improvement of two important production traits of pigs through site-directed single gene manipulation not only lays a foundation for the application and basic research of genetic editing for big animals, but also provides with breeding researchers a new way of thinking for improving traits of livestock. The transgenic pig and the preparation method thereof have good economic value and application prospects.

What is claimed is:

1. A transgenic pig whose genome comprises a nucleic acid sequence encoding uncoupling protein 1 (UCP1) operably linked to an adiponectin promoter inserted into an endogenous UCP1 gene, wherein the pig is leaner and more resistant to cold than a wild-type pig.

2. The transgenic pig according to claim 1, wherein the UCP1 gene is a mouse UCP1 gene.

3. The transgenic pig according to claim 1, wherein the adiponectin promoter is a mouse adiponectin promoter.

4. A method of making a transgenic pig that is leaner and more resistant to cold, the method comprising:
   a) constructing a donor plasmid encoding uncoupling protein 1 (UCP1) operably linked to an adiponectin promoter;
   b) constructing a vector encoding Cas9 and a guide RNA (gRNA) that targets exon 2 of a pig UCP1 gene;
   c) co-transfecting isolated fetal pig fibroblasts with the donor plasmid, the vector, and the gRNA;
   d) cloning the fibroblasts obtained in step c);
   e) screening the cloned fibroblasts for the donor plasmid by PCR;
   f) transferring the nucleus of a fibroblast containing the donor plasmid screened in step e) into an enucleated pig oocyte such that a transgenic pig whose genome comprises a nucleic acid sequence encoding uncoupling protein 1 (UCP1) operably linked to a adiponectin promoter inserted into an endogenous UCP1 gene is obtained, wherein the pig is leaner and more resistant to cold than a wild-type pig.

5. The method according to claim 4, wherein the donor plasmid is derived from a pLB vector.

* * * * *